United States Patent [19]

Ochi

[11] Patent Number: 5,364,636
[45] Date of Patent: Nov. 15, 1994

[54] INHIBITOR OF ABSORPTION OF DIGESTION PRODUCT OF FOOD AND DRINK

[75] Inventor: Shigeo Ochi, Tokyo, Japan

[73] Assignee: Hanabusa Patent Office, Tokyo, Japan

[21] Appl. No.: 844,628

[22] PCT Filed: Oct. 2, 1990

[86] PCT No.: PCT/JP90/01270

§ 371 Date: Apr. 1, 1992

§ 102(e) Date: Apr. 1, 1992

[87] PCT Pub. No.: WO91/04751

PCT Pub. Date: Apr. 18, 1991

[30] Foreign Application Priority Data

Oct. 2, 1989 [JP] Japan ................................ 1-257229

[51] Int. Cl.$^5$ .............................................. A61K 9/64
[52] U.S. Cl. .................................... 424/456; 424/451; 424/491; 424/492; 424/493; 424/494; 424/495; 514/866; 514/892; 514/909; 514/911
[58] Field of Search ............... 424/451, 456, 491, 492, 424/493, 494, 495; 514/909, 911

[56] References Cited

U.S. PATENT DOCUMENTS

| 4,444,761 | 4/1984 | Spiller | 424/180 |
| 4,695,466 | 9/1987 | Morishita et al. | 424/456 |

FOREIGN PATENT DOCUMENTS

| 0050347 | 4/1982 | European Pat. Off. |
| 0319645 | 6/1989 | European Pat. Off. |
| 63-105474 | 5/1988 | Japan |
| 64-52713 | 2/1989 | Japan |
| WO88/09162 | 12/1988 | WIPO |

*Primary Examiner*—Thurman K. Page
*Assistant Examiner*—Jyothsna Venkat
*Attorney, Agent, or Firm*—Oliff & Berridge

[57] ABSTRACT

A drug for preventing the absorption of food materials dissolved during digestion, a drug for preventing obesity, a drug for treating hyperlipemia, a drug for treating diabetes mellitus, and a drug for preventing constipation, wherein the flocculant and other auxiliary additives at request, are coated with the aquatic enteric material.

6 Claims, 4 Drawing Sheets

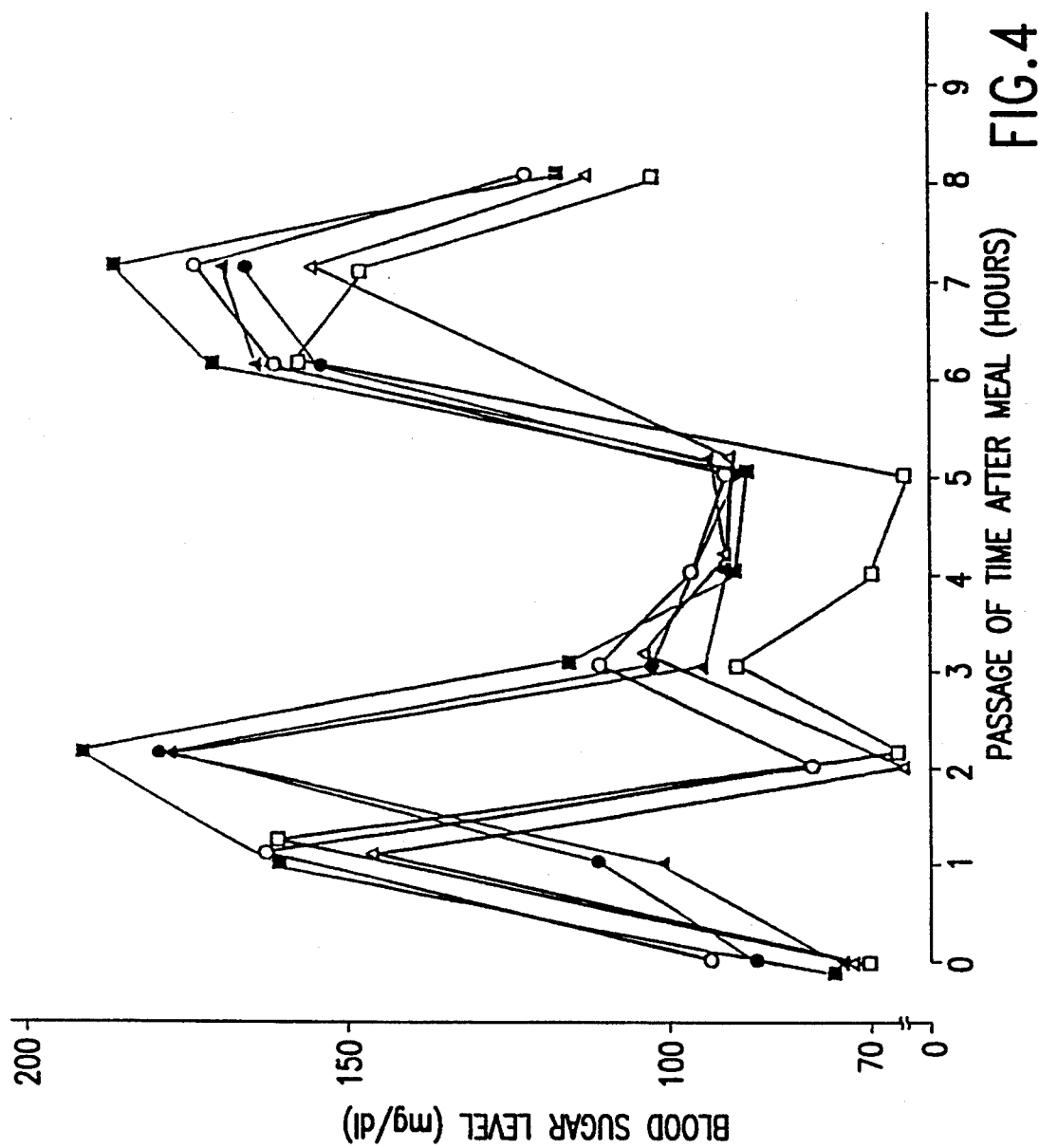

INHIBITOR OF ABSORPTION OF DIGESTION PRODUCT OF FOOD AND DRINK

FIELD OF THE INVENTION

This invention pertains to a drug for preventing the absorption of food materials dissolved during digestion, as well as a drug for preventing obesity, a drug for treating hyperlipemia, a drug for treating diabetis mellitus, and a drug for preventing constipation.

BACKGROUND OF THE INVENTION

In recent years when a great variety of foodstuffs are available abundantly, people of these days are inclined to intake excessive nutrition, and this causes obesity. For this reason, some young women minimize their intake of food in the hope of avoiding becoming obese.

However, this can cause the problem of unbalanced food intake, often causing a variety of physiological and psychological problems, such as sitiophobia and the resulting overeating.

It is generally considered that self-control of eating is desirable for preventing to be obese, but it is almost impracticable to voluntarily give up the intake of tasty food in these days, the age of gourmet.

To solve this problem, use of the reducing drugs has been proposed. In European countries and the United States, for example, Fenfluramine, Fluoxetine and other drugs are now commercially available, and Mazindol (Sandoz Pharmaceutical Ltd., Switzerland) for inhibiting the desire to eat, has also been developed. However, these are medical pharmaceuticals directly or indirectly acting upon the alimentary center and the satiety center of hypothalamus in the brain, and hence their adverse effects are unavoidable. In addition, the efficacy of these pharmaceuticals may decrease upon repeated administrations.

It is known that excessive intake of nutrition causes obesity, and sometimes leads to the so-called adult diseases, such as diabetes mellitus, heart disease and apoplexy. It has been reported that foodstuffs, that cause lipid production including cholesterol and neutral fat (triglycerides), are involved in the occurrence of cerebrovascular disorders, namely, arterioscelrosis and heart disease.

Furthermore, the increased occurrence of adult diseases in the younger generation resulting from excessive intake of nutrition has become a social problem.

It is reasonable to say that food should be restricted to prevent excessive intake of nutrion. However, various limitations of foodstuffs thus required mean the limitation of cuisine, and this gives housewives a great deal of extra labor.

When one of the family members might be at the risk of becoming obese or falling victim to an adult disease, a housewife must prepare special food, in addition to the ordinary food for the other family members. This gives her a great burden.

This stimulated the realization that fattening foodstuffs, even if taken in excessive amounts, would not cause obesity or adult disease if the excess portion of the nutritive food materials dissolved during digestion were excreted without absorption by the body.

This concept has already resulted in the applicant's invention of a drug for preventing the absorption of food materials dissolved during digestion (Japan Patent Application No. 105474 in 1988), which is characterized by the oral administration of a cavity device that allows a certain amount of the dissolved food material to be efficiently excreted with the feces.

Although the aforementioned cavity device is fairly effective, the excretion of the dissolved food material is limited, because the dissolved food material is incorporated into the aforementioned cavity device. A permeable membrane or a membrane having a valve is required for the preparation of the aforementioned cavity device. This involved problems of the difficulty in manufacturing and a high production cost.

PRESENTATION OF THE INVENTION

The purpose of the present invention is to solve the problems described above, i.e., to provide a device for preventing the absorption of food materials dissolved during digestion, which is able to coagulate the excessive nutrients, thereby excreting the dissolved food materials outside the body without absorption by the body. A further object of this investion is to provide a preventive for obesity, a remedy for hyperlipemia, a remedy for diabetes mellitus and a preventive for constipation, each utilizing the effect of preventing the absorption of food materials dissolved during digestion as described above.

The drug for preventing the absorption of food materials dissolved during digestion of this invesntion is characterized by comprising an aquatic enteric coating, a flocculant and an auxiliary additive at request, wherein all the components other than the aquatic enteric coating are covered with the aquatic enteric material to achieve the aforementioned objects.

This invention also relates to a drug for preventing obesity (antiobesic), a drug for preventing hyperlipemia (hyperlipemic remedy to control lipid components in hyperlipemia), a drug for preventing diabetes mellitus (diabetic remedy to control blood-sugar components in diabetes mellitus) and a drug for preventing constipation (laxative), in the composition as described above. (The dissolved food materials absorption inhibitor, the antiobesic, the hyperlipemic remedy, the diabetic remedy, and the laxative described above are hereinafter referred to as the drug of this invention.)

The term aquatic enteric coating herein means a substance soluble in the third stage of stomach (pylorus), in the small intestine or in the large intstine, for example, cellulose, chitin and chitosan derivatives, such as hydroxypropylmethyl cellulose acetate/succinate, hydroxypropylmethyl cellulose phthalate, cellulose acetate/phthalate and carboxymethylethyl cellulose.

The flocculant is a harmless compound capable of coagulating the dissolved food material in the intestinal tract to form the larger flocs. As typical examples, sodium polyacrylate, sodium alginate, Guar gum, starch, sodium salt of carboxymethyl cellulose (CMC), gelatin and chitosan, can be named, which may be employed either singly or in combination.

As the auxiliary additive to be contained in the drug of this invention at request, any substances harmless to the human body can be used, but a substance which serves to improve the effect of the drugs of this invention should preferably be used. As typical examples of such substances, fibrous materials, namely natural fiber as cotton fiber and dietary fiber, as well as adsorbents, such as activated charcoal, activated alumina, silica gel, bentonite, zeolite, diatomaceous earth, aluminum silicate, calcium carbonate, ceramics, ceramic materials, chitin, chitosan, perlite materials and attapulgite, can be used. The aforementioned fibrous materials are desirable because of their effects to accelerate floc formation of the aforementioned dissolved food materials in the intestinal tract and to stabilize the structure of the formed flocs. In addition, the aforementioned fibrous materials and adsorbents are useful to give additional effect on the drug of this invention by adsorbing and discharging the harmful substances in the foodstuffs and harmful mattters yielded in the course of metabolism.

The drug of this invention may be employed in any dosage forms, but preferably the following forms shall be employed.

- A form wherein all the components other than the aquatic enteric coating (i.e., a flocculant and, in some cases, an auxiliary additive) are enclosed in capsules made of aquatic enteric material.
- A form wherein the flocculant is directly coated with the aquatic enteric material.

In the above dosage forms, the flocculant should preferably be granules, especially those having a diameter in the range from about 0.1 to 0.5 mm. Alternatively, the flocculant may also be in the form of particles made of aggregates composed of its fine powder.

In the former dosage form listed above, the flocculant may also be enclosed in microcapsules, which are then enclosed in capsules of ordinary size (No. 00 to No. 5). It is necessary in this case that at least either one of the microcapsules or the ordinary capsules is made of the aquatic enteric material. When an auxiliary additive is also contained, this may be enclosed in the aforementioned microcapsules for the flocculant or in separate microcapsules, or this may be directly enclosed in the ordinary capsules, without being enclosed in microcapsules, if these ordinary capsules are made of the aquatic enteric material. The term capsule used in this specification means an ordinary capsule or a microcapsule, unless otherwise specified.

In the latter dosage form listed above, when the flocculant is granules or aggregates composed of fine powder (hereinafter referred to as granules, etc.), it is preferable that each of the granules, etc., be directly coated with aquatic enteric material, and these granules, etc., may be enclosed in capsules (which may not be made of the aquatic enteric material but also be made of common gelatin). In addition, when an auxiliary additive is also contained, it is preferable that this auxiliary additive shall also be coated directly with the aquatic enteric material.

It is particularly preferable that the drug of this invention contain the components as listed below so that the flocculant will gradually be exposed and dissolved in the third stage of the stomach (pylorus) or in the succeeding stages in the digestive tract.

- A mixture of flocculant particles in various particle sizes.
- A mixture of microcapsules made of different kinds of aquatic enteric materials which are soluble at different pH levels.
- A mixture of flocculant particles with different degrees of coat thickness, or a mixture of flocculant particles coated with different kinds of aqueous enteric materials which are soluble at different pH levels, when the flocculant is directly coated with the aquatic enteric material.

In addition, the flocculant particles enclosed in microcapsules and those directly coated with the aquatic enteric material may also be enclosed in the same capsule.

Furthermore, the capsules used for the drug of this invention may be coated with a sweetening component, a confectionery material or a flavor.

The drug of this invention is orally administered before a meal, after a meal, and/or during a meal. The propoer dose may be different according to the food intake and the symptoms of the patient to be treated, as well as the kinds of flocculant and auxiliary additives contained therein; when sodium polyacrylate is used as the flocculant, the dose should preferably be such as that the intake of the aforementioned flocculant will be within the range of about 0.5 to 2 g/day.

When the dissolved food material absorption inhibitor of this invention which has the composition as described above, is orally administered, it passes through the first and second stages of the stomach (cardia and corpus) as it is, and the aquatic enteric coating is dissolved for the first time when the drug reaches the third stage of the stomach (pylorus) or the upper part of the small intestine (duodenum or jejunum), thus the flocculant is exposed to be dissolved. This flocculant then coagulates the dissolved food material present in the third stage of the stomach, or in the upper part of the small intestine and onwards, forming gruel-like aggregates with a gelatinous surface. Such aggregates are formed, because a certain amount of the flocculant converts the dissolved food material into gruel-like aggregates, and another part of the residual flocculant then adheres to the surface of the aforementioned aggregates, thus forming a slimy surface like gelatin. Such aggregates are effectively formed particularly when the flocculant is gradually exposed and dissolved in the third stage of the stomach, in the small intestine or in the large intestine.

The dissolved food material converted into such aggregates is hardly subjected to the actions of bile acid and digestive enzymes, and hence their absorption through the intestinal wall during the passage from the small intestine to the large intestine, particularly in the jejunum (the major part of absorption) is inhibited. Accordingly, a definite amount of the dissolved food material corresponding to the amount of the drug of this invention administered is discharged out of the body without being absorbed in the body.

Thus, the drug of this invention also serves as an antiobesic, because a definite amount of foodstuffs is discharged without being absorbed in the body as described above.

Furthermore, the aforementioned aggregate, which is composed of gruel-like contents with a gelatinous coat, smoothly passes through the intestinal tract, showing no adverse effect upon the normal transfer of the foodstuffs in the intestines of healthy persons (segmenting movement and peristalsis). Hence, such aggregates do not disturb excretion of the foodstuffs but rather accelerate defecation to prevent constipation. In addition, if a fibrous material is contained as an auxiliary additive, it serves as a nucleus in formation of the aggregte, thus ensuring its formation and accelerating defecation, the effect of foodstuff excretion is further enhanced.

The remedies of this invention for hyperlipemia and for diabetes also work in the same way as above; as a result of inhibited absorption of the dissolved food material, absorption of cholesterol, neutral fat and sugars into blood through the intestinal wall is also inhibited, preventing the increase in amount of lipid and sugar in blood.

SIMPLE EXPLANATION OF DRAWINGS

FIGS. 1 through 4 show changes in amount of various components in the serum on the day when the drug of this invention was administered and on the preceeding day. FIGS. 1 through 4 show the amount of triglyceride, betalipoprotein, cholesterol, and blood sugar respectively.

In these figures, the thin lines show the values on the preceeding day, and the bold lines show the values on the day of administration.

DETAILED DESCRIPTION OF THE INVENTION

Figure 1:
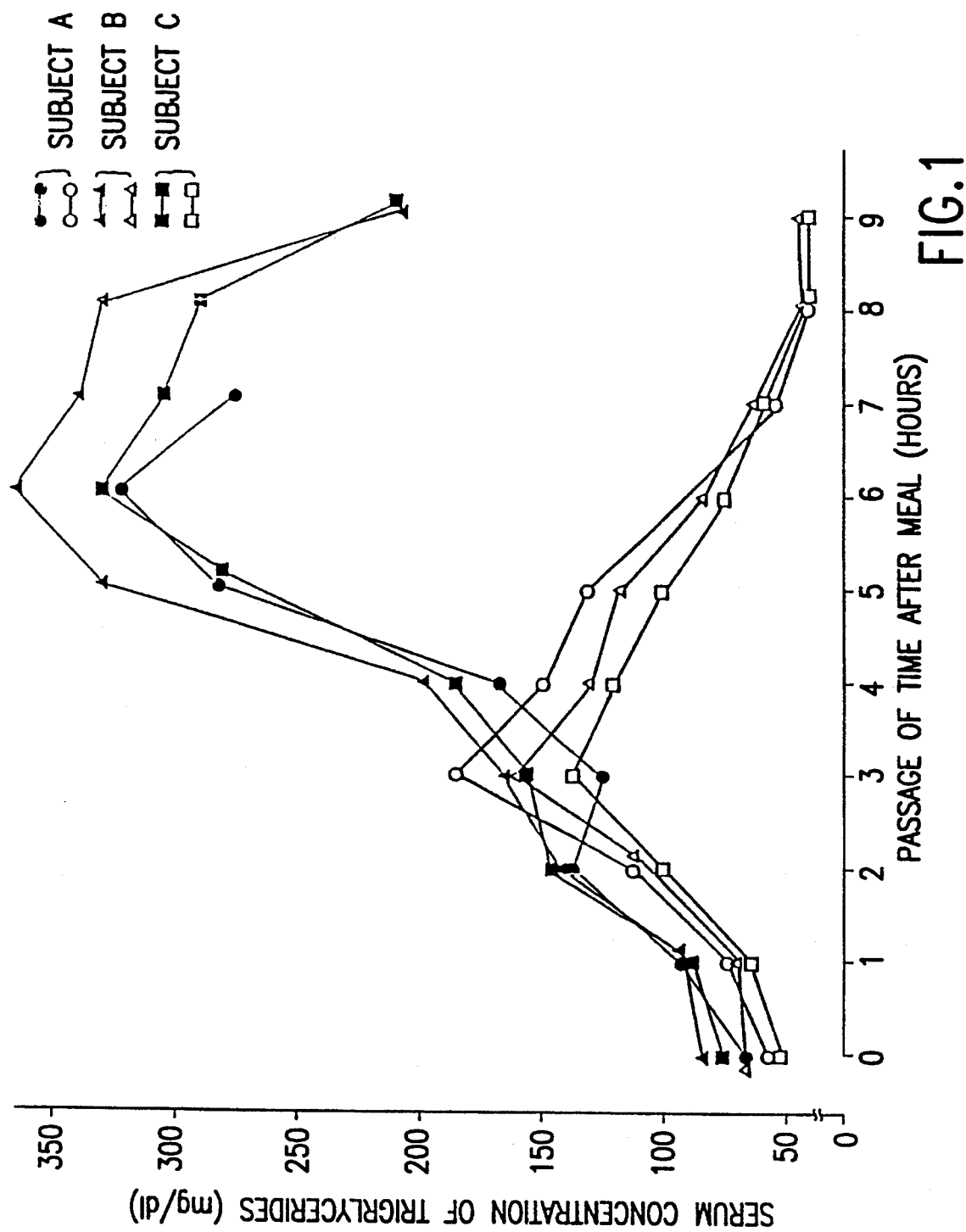

The following examples are to explain this invention in detail, not to limit its scope.

EXAMPLE 1

Acqueous Enteric Material—Flocculant (a) Granules of sodium polyacrylate with an appropriate particle size are used as the flocculant, which are enclosed in microcapsules made of an aquatic enteric material, namely, hydroxypropylmethyl cellulose acetate/succinate, and a proper number of these microcapsules are then enclosed in capsules of ordinary size (No. 00 to No. 5) made of gelatin or the like.

The particle size of flocculant, its amount based on the weight of microcapsules and on the total weight of capsules, as well as the sizes of these capsules, may be selected appropriately. An aggregate of fine particles or a mixture with other types of flocculant, may be used as the flocculant. As to the microcapsules, too, a mixture of different materials may be used if it shows the aquatic enteric activity.

Separately from the above, microcapsules made of gelatin or the like and ordinary capsules made of an aquatic enteric material may be used in combination, or both kinds of capsules may be made of an aquatic enteric material. However, when dispersion of the drug of this invention is taken into consideration, the former combination (microcapsules made of an aquatic enteric material and ordinary capsules made of gelatin or the like) is preferable, because individual microcapsules uniformly dispersed in the food present in the stomach reach the third stage of the stomach or the upper part of the small intestine, where these microcapsules are dissolved to expose the flocculant, and hence all of the foodstuff involved form flocs, therby the absorption of the dissolved food material can be inhibited more effectively.

When using microcapsules made of an aquatic enteric material, it is particularly preferable to adopt the plans listed below in order to ensure the exposure and dissolution of the flocculant in various stages following the third stage of the stomach in the digestive tract (hereinafter referred to as the delayed dissolution of the flocculant).

(1) Use of microcapsules with various thickness levels, or microcapsules made of various aquatic enteric materials, which dissolve at various pH levels, or (2) Use of a flocculant with various particle sizes.

Consequently, the flocculant is gradually exposed and dissolved in various stages after the third stage of the stomach in the digestive tract. Firstly foodstuff aggregates are gradually formed according to the dissolution of flocculant, and gelatinous membranes are then formed on the surface of these aggregates by the flocculant dissolved later to prevent penetration of digestive enzymes and bile acid, thus forming aggregates that are not absorbed through the intestinal walls. Formation of such aggregates occurs in various stages after the third stage of the stomach in the digestive tract enabling to flocculate different kind of components in degradation products and metabolites in various parts of the intestinal tract, which ensures the more effective control of the dissolved food material absorption and smooth excretion.

It is needless to say that the same satisfactory results can be achieved even when the above-described microcapsules are not used and the flocculant is enclosed in ordinary-size capsules made of an aquatic enteric material.

It is also possible, in any mode of drugs described above, to form sugar coating on the surface of the ordinary size capsules or to coat the surface with a confectionery material or a flavor, thereby even children are able to swallow the drugs comfortably.

(b) Each granule of sodium polyacrylate used in the above paragaraph (a) is directly coated with the aquatic enteric material. This is effected by spraying an acetone solution of hydroxypropylmethyl cellulose acetate/succinate to the suspended granules of the flocculant and drying them to eliminate the solvent. Each granule is thus coated with a film of the aquatic enteric material.

The thicknes and physical strength of the coated film may be appropriately adjusted by the manufacturing conditions. In addition, if flocculant granules with different thickness levels of coating, different kinds of film (different pH levels at which the aquatic enteric material is dissolved), different levels of physical strength and differnt levels of particle size are mixed together, the drug of this invention exhibiting the unique effect caused by the flocculant's delayed dissolution in the intestines as described in the above paragraph (a) can be obtained. It is also possible to obtain a drug which acts in a certain definite region by enclosing a flocculant that can be exposed at a specific region in the capsule.

Aquatic enteric material other than hydroxypropylmethyl cellulose acetate/succinate may also be employed in a similar way by selecting a proper solvent, but it is necessary, in this case, to adopt a solvent that does not dissolve the flocculant employed.

The coated granules thus obtained can be easily administered if enclosed in capsules. The capsules used for this purpose need not always be made of the aquatic enteric material; these may be made of gelatin or the like, or man be coated with a sweetening component or the like.

The particle size of flocculant, its amount based on the weight of capsules, and the size of capsules are selected appropriately also in this case, and the flocculant may be used as aggregates of the fine powder taking place of granules.

When a drug of this invention in this type is orally administered, each of the flocculant granules (or aggregates of fine powder) coated with the aquatic enteric material is dispersed in the food present in the first or second stage of the stomach, and the dispersion thus formed reaches the pylorus or the upper part of the small intestine, where individual particles of the flocculant are exposed and form flocs of the dissolved food material. Thus, basically, the effect of inhibiting absorption of the whole foodstuff taken in can be expected uniformly corresponding with the amount of drug administered.

As the flocculant to be used in the drug of this line, those in the form of tablets directly coated with the aquatic enteric material may also be employed. In this case, however, it is preferable that the tablets are in a form capable of being dispersed effectively in the stomach in order to ensure fine dispersion of the drug in the stomach.

(c) Flocculants described in the above paragraphs (a) and (b) are both enclosed in a capsule.

It is preferable in this case that the uncoated and coated flocculants each enclosed in microcapsules made of the aquatic enteric material, are further enclosed in ordinary capsules made of gelatin or the like. However, it is needless to say that similar results can be achieved even when the uncoated and coated flocculants each enclosed in microcapsules made of gelatin or the like are further enclosed in ordinary capsules made of the aquatic enteric material, or when the uncoated and coated flocculants not enclosed in microcapsules are directly enclosed in ordinary capsules made of the aquatic enteric material.

It is also preferable in any of these cases to achieve the effect of flocculant's delayed dissolution; and the outermost capsule may also be coated with a sweetening component, a confectionery material or a flavor.

EXAMPLE 2

Aquatic Enteric Material—Flocculant—Auxiliary Additive (a) The same granules of sodium polyacrylate as used in the paragraph (a) of Example 1 are employed as flocculant, which are enclosed, together with cotton fibers (0.5 to 2 mm in length and 0.5 to 1 mm in diameter) as an auxiliary additive, in aquatic enteric microcapsules made of hydroxypropylmethyl celulose acetate/-succinate, and a proper number of these microcapsules are then enclosed in ordinary-size capsules made of gelatin or the like.

The cotton fibers are employed after being immersed in 10% aqueous solution of $CaCl_2$ and dried. Use of such cotton fibers with Ca ions adhered thereto is preferable, because these are adsorbable in the body and easily combined with the flocculant, further ensuring the formation of foodstuff flocs, and these are also easily combined with the flocs thus formed, thereby forming the larger flocs and adsorbing the harmful substances contained in the dissolved food material.

The particle size of the flocculant, its amount based on the weight of microcapsules and of the total capsules, the kind and amount of the auxiliary additive, and the size of these capsules may be appropriately selected. The flocculant may be used as aggregates of its fine powder, or as a mixture with other kind of flocculant, and the auxiliary additive may be used as a mixture of different substances. The microcapsules may also be a mixture of different kinds insofar as these are of all aquatic enteric materials.

Furthermore, the microcapsules made of gelatin or the like may be used together with ordinary capsules made of the aquatic enteric material, or the microcapsules and ordinary capsules both made of the aquatic enteric material may also be used. However, when the dispersion effect of the drug of this invention in the stomach as described in the paragraph (a) of Example 1 is taken into consideration, the former combination (microcapsules made of an aquatic enteric material and ordinary capsules made of gelatin or the like) is more preferable.

It is also a practical way that microcapsules, in which only the flocculant is enclosed, are then enclosed in ordinary size capsules, and the auxiliary additive is enclosed in separate ordinary-size capsules made of the aquatic enteric material.

The flocculant and the auxiliary additive may also be enclosed in same or separate capsules of ordinary size made of the aquatic enteric material, without using the microcapsule as described above.

Also in this case, it is preferable to achieve the effect of flocculant's delayed dissolution as described in the above examples.

In the same manner the ordinary size capsules for any mode of drugs described above may be sugar coated, or also coated with a confectionery material or a flavor.

(b) Each of the sodium polyacrylate granules described in the above paragraph (a) is directly coated with the aquatic enteric material in the same way as in the paragraph (b) of Example 1, and these coated granules are then enclosed in capsules together with the same auxiliary additive as used in the above paragraph (a), thus giving a drug which can be easily administered. The capsules used in this case need not be those made of the aquatic enteric material, and may be those made of gelatin or the like. A sweetening component or the like may also be coated on the surface.

The auxiliary additive may also be enclosed in separate capsules from those containing the flocculant.

The cotton fibers used as the auxiliary additive may be directly coated with an aquatic enteric material, and it is preferable that the cotton fibers are immersed in an aqueous solution of $CaCl_2$ and dried, prior to the coating with the respective aquatic enteric material. As the auxiliary additive, fibrous materials other than cotton fibers or an adsorbent (for example, activated charcoal) may also be used, and it is also preferable to coat them directly with the aquatic enteric material.

The drugs of this type are also dispersible in the first or second stage of the stomach as described in the paragraph (b) of Example 1.

Also in this series, it is preferable to achieve the effect of flocculant's delayed dissolution as described in the aforementioned examples.

(c) The flocculant and auxiliary additive described in the above paragraphs (a) and (b) of Example 2 are enclosed in a capsule.

What is preferable in this case is that microcapsules made of the aquatic enteric material, in which the uncoated flocculant and the uncoated auxiliary additive are enclosed, are further enclosed, together with the coated flocculant and the coated auxiliary additive in ordinary capsules made of gelatin or the like. However, it is needless to say that similar results can be achieved even when microcapsules made of gelatin or the like, in which the uncoated flocculant and the uncoated auxiliary additive are enclosed, are further enclosed, together with the coated flocculant and the coated auxiliary additive, in ordinary capsules made of the aquatic enteric material; when the uncoated flocculant and the uncoated auxiliary additive (not enclosed in microcapsules) are directly enclosed in ordinary capsules made of an aquatic enteric material together with the coated flocculant and the auxiliary additive; or when the auxiliary additive is enclosed in microcapsules or ordinary capsules separately from those for the flocculant.

Also in this series, it is preferable to achieve the effect of flocculant's delayed dissolultion, and the surface of the outermost capsules may also be coated with a sweetening component, a confectionery material or a flavor.

Test Example

To three healthy adults (Subjects A, B and C) who took in the calorific food (4000 kcal), the drug of this invention was orally administered during the meal, and the changes in amounts of triglyceride, beta-lipoprotein, cholesterol and blood sugar in the serum of these subjects were measured with the passage of time.

The amounts of these components in the serum of these subjects who took in the same amount of the same food as above on the day before the drug administration, were measured in comparison.

The administered drug was the one described in the paragraph (b) of Example 2, in which the particle size of the flocculant (sodium polyacrylate) was about 0.5 mm, the dose was 0.05 g/kg.body-weight, the amount of cotton fibers used as the auxiliary additive (treated with $CaCl_2$ and then coated with the aquatic enteric material) was about 0.02 g/kg.body-weight, and the flocculant and cotton fibers were enclosed in separate capsules both made of gelatin.

Blood samples were taken from the subjets before meal, as well as 30 minutes, 1 hour, 1.5 hours and 2 hours after meal, and after that at intervals of 1 hour for 8 or 9 hours after administration.

Figure 2:
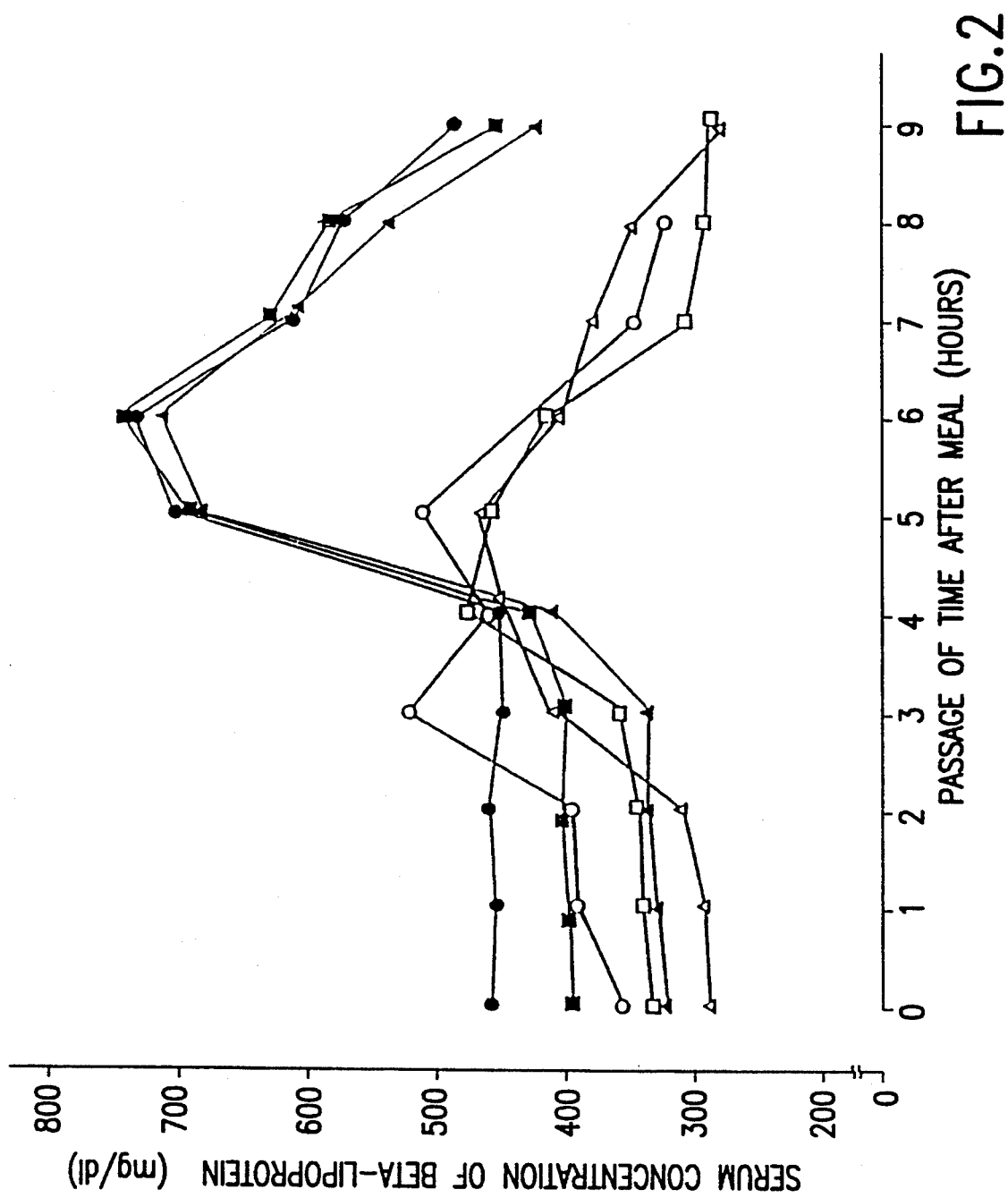
Figure 3:
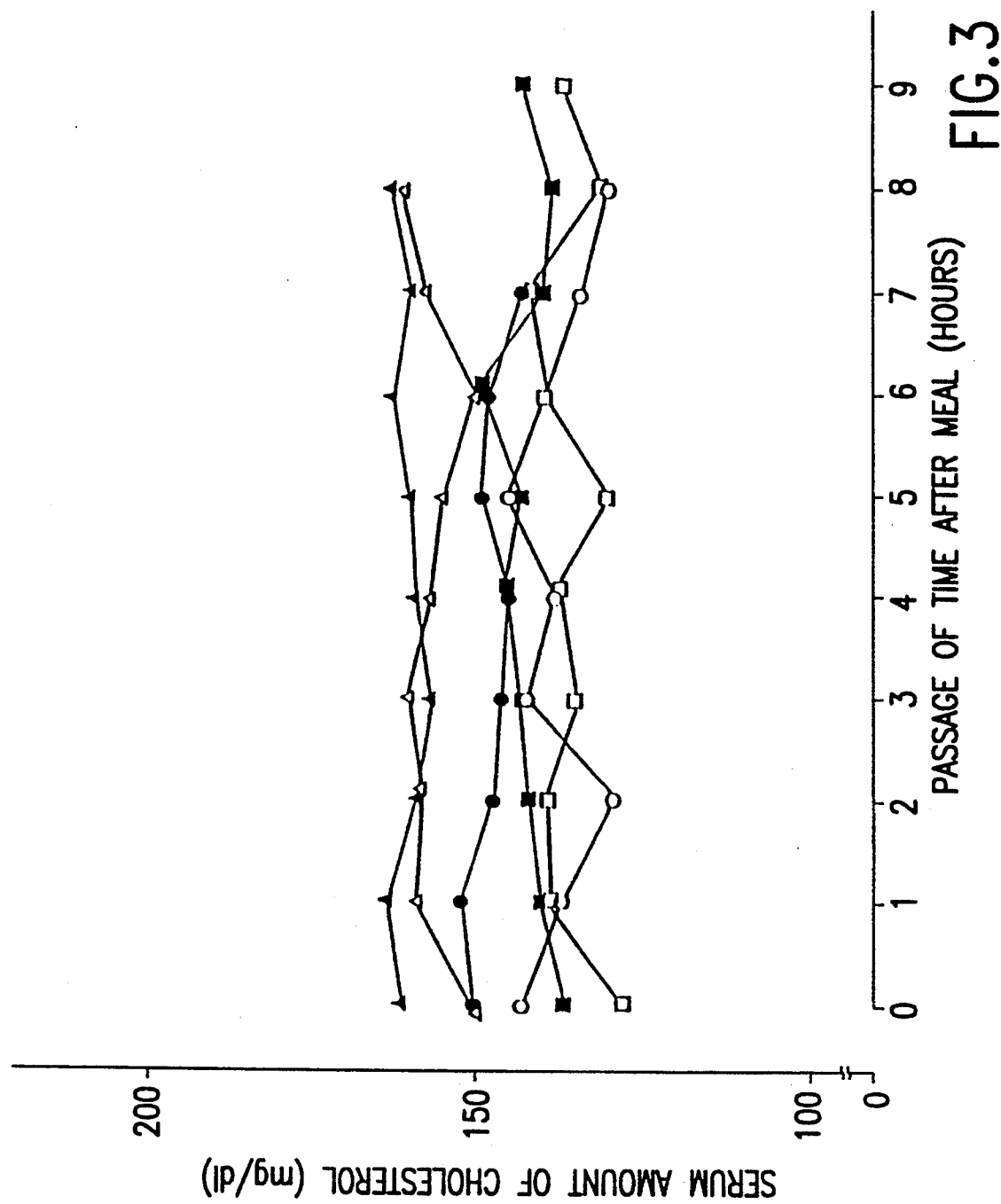

The results obtained are illustrated in FIGS. 1 through 4, in which FIG. 1 shows the amount of triglyceride, FIG. 2 shows the amount of beta-lipoprotein, FIGS. 3 shows the amount of cholesterol, and FIG. 4 shows the changes in the blood sugar level on the day before drug administration and on the day of drug administration. In these fiures, the black marks linked with thin lines show the changes on the day before drug administration, and the blank marks linked with bold lines show the changes on the day of drug administration. Circular marks (o,  ) are the data with Subject A, triangular marks (Δ,  ) are the data with Subject B, and square marks (□,  ) are the data with Subject C.

These fiures indicate that the increase in the amounts of triglyceride (FIG. 1) and beta-lipoprotein (FIG. 2) in the serum was markedly inhibited and that the increase in the amounts of cholesterol (FIG. 3) and blood sugar (FIG. 4) was also inhibited, only slightly though. The amount of cholesterol in the blood increased or decreased very slowly for the long passage of time, and hence the effect of food intake is considered to be very slight.

Industrial Potential of the Invention

As explained above in detail, the drug for preventing the absorption of food materials dissolved during digestion (dissolved food material absorption inhibitor), the preventive for obesity (antiobesic), the remedy for hyperlipemia (hyperlipemic remedy), the remedy for diabetes mellitus (Diabetic remedy), and the preventive for constipation (laxative) of this invention are to inhibit absortion of the dissolved food material through the intestinal walls to a certain degree by administration before, affter and/or during the meal. Hence, absorption of excessive nutrients can be prevented without restriction of food intake, and in its turn preventing obesity as well. The increase in amount of lipids and sugars in blood can also be prevented. Accordingly, repeated administration of a drug of this invention ensures its effect on prophylaxis as well as treatment of obesity and adult diseases.

In addition, the dissolved food material passes through the intestinal tract as a gruel-like aggregate covered with the gelatinous film, which results in smooth defecation to prevent constipation by reducing retention time of the dissolved food material. It is generally known that a long stay of foodstuffs in the intestines is one of the risk factors of large bowel cancers, therefore, the drug of this invention is expected to exhibit the effect of preventing large bowel cancers.

In addition, the dissolved food material absorption inhibitor of this investion does not act mainly on the alimentary center and satiety center of hypothalamus in the brain unlike the so-called reducing drugs, but physically discharges the foodstuffs outside the body; hence, no danger of adverse reaction is expected.

Simultaneously, the hyperlipemic remedy and the diabetic remedy of this invention do not cause any adverse reactions as conventionally used drugs.

The drug of this invention is further provided with various effects by containing an auxiliary additive together with the flocculant. For example, use of fibrous materials as the auxiliary additive accelerates flocculation and discharge of foodstuffs, and use of an adsorbent, such as activated charcoal, provides the effect of adsorbing the harmful additives contained in the food, or harmful matters formed in the course of metabolism, in the aggregates of dissolved food materials and discharge them accordingly.

Furthermore, the drug of this invention can easily be prepared with no need of using specific materials.

What is claimed is:

1. A dissolved food material absorption inhibitor, comprising (1) a flocculant selected from the group consisting of sodium polyacrylate, sodium alginate, and gelatin, and (2) an auxiliary additive selected from the group consisting of natural fibers, dietary fibers and adsorbents, said (1) flocculent and (2) auxiliary additive coated with (3) an aquatic enteric material selected from the group consisting of cellulose, chitin and chitosan derivatives.

2. The dissolved food material absorption inhibitor as defined in claim 1, wherein sodium polyacrylate is used as the flocculant.

3. The dissolved food material absorption inhibitor as defined in claim 1, wherein all the components other than the aquatic enteric material are contained in aquatic enteric capsules.

4. The dissolved food material absorption inhibitor as defined in any of claim 1, wherein fibrous materials are used as the auxiliary additive.

5. The dissolved food material absorption inhibitor as defined in claim 1, wherein the cellulose aquatic enteric coating material is selected from the group consisting of hydroxypropylmethyl cellulose acetate, hydroxypropylmethyl cellulose succinate, hydroxypropylmethyl cellulose phthalate, cellulose acetate, cellulose phthalate and carboxymethylethyl cellulose.

6. The dissolved food material absorption inhibitor as defined in claim 1, wherein the auxiliary additive is selected from the group consisting of cotton fiber, activated charcoal, activated alumina, silica gel, bentonite, zeolite, diatomaceous earth, aluminum silicate, calcium carbonate, ceramics, ceramic materials, chitin, chitosan, perlite materials and attapulgite.

* * * * *

UNITED STATES PATENT AND TRADEMARK OFFICE
CERTIFICATE OF CORRECTION

PATENT NO. : 5,364,636

DATED : November 15, 1994

INVENTOR(S) : Shigeo Ochi

It is certified that error appears in the above-identified patent and that said Letters Patent is hereby corrected as shown below:

On the title page, item [56], under References Cited, insert the following:
```
61-143321   7/86    Japan
 2504801    5/82    France
57-146713   3/81    Japan
63-308001  12/88    Japan
62-201821   9/87    Japan
```

Signed and Sealed this

Fifth Day of September, 1995

BRUCE LEHMAN

*Attest:*

*Attesting Officer*          Commissioner of Patents and Trademarks

UNITED STATES PATENT AND TRADEMARK OFFICE
CERTIFICATE OF CORRECTION

PATENT NO.    : 5,364,636
DATED         : November 15, 1994
INVENTOR(S)   : Shigeo Ochi It is certified that error appears in the above-identified patent and that said Letters Patent is hereby corrected as shown below:

On the title page, item [73] Assignee, should be deleted.

Signed and Sealed this

Twenty-eighth Day of May, 1996

*Attest:*

BRUCE LEHMAN

*Attesting Officer*    *Commissioner of Patents and Trademarks*